United States Patent [19] [11] 4,128,537
Markiewitz [45] Dec. 5, 1978

[54] PROCESS FOR PREPARING ETHYLENICALLY UNSATURATED ISOCYANURATES

[75] Inventor: Kenneth H. Markiewitz, Wilmington, Del.

[73] Assignee: ICI Americas Inc. Wilmington, Del.

[21] Appl. No.: 819,352

[22] Filed: Jul. 27, 1977

[51] Int. Cl.$^2$ .......................................... C08G 18/00
[52] U.S. Cl. ..................................... 528/49; 544/222; 528/55; 528/75; 528/51
[58] Field of Search ................ 544/222; 260/77.5 NC, 260/77.5 AB

[56] References Cited

U.S. PATENT DOCUMENTS

| | | | |
|---|---|---|---|
| 2,894,950 | 7/1959 | Lloyd et al. | 260/77.5 NC |
| 2,947,736 | 8/1960 | Lundberg | 260/77.5 |
| 2,952,665 | 9/1960 | Bunge et al. | 260/77.5 |
| 2,958,704 | 11/1960 | Dinbergs et al. | 260/468 |
| 3,041,313 | 6/1962 | Lavin et al. | 260/67 |
| 3,061,591 | 10/1962 | Roth | 260/75 |
| 3,065,231 | 11/1962 | Frazier et al. | 260/77.5 NC |
| 3,154,522 | 10/1964 | Beitchman | 260/77.5 |
| 3,168,483 | 2/1965 | Beitchman et al. | 252/426 |
| 3,252,942 | 5/1966 | France | 260/77.5 |
| 3,297,745 | 1/1967 | Fekete et al. | 260/471 |
| 3,437,500 | 4/1969 | Hennig et al. | 106/252 |
| 3,450,648 | 6/1969 | Windemuth et al. | 260/77.5 AB |
| 3,609,149 | 9/1971 | Matsui et al. | 260/248 NS |
| 3,642,943 | 2/1972 | Noel et al. | 260/859 R |
| 3,658,801 | 4/1972 | Berry et al. | 260/248 NS |
| 3,658,801 | 4/1972 | Berry et al. | 260/77.5 NC |
| 3,694,415 | 9/1972 | Honda et al. | 260/77.5 CR |
| 3,719,638 | 3/1973 | Huemmer et al. | 260/77.5 CR |
| 3,723,367 | 3/1973 | Chow et al. | 260/2.5 AB |
| 3,763,269 | 10/1973 | Formaini | 260/75 UA |
| 3,786,030 | 1/1974 | Rice | 260/77.5 NC |
| 3,821,067 | 6/1974 | Taylor et al. | 260/37 N |
| 3,821,098 | 6/1974 | Garratt et al. | 204/159.22 |
| 3,840,618 | 10/1974 | DaFano | 260/863 |
| 3,849,349 | 11/1974 | Frisch et al. | 260/2.5 AW |
| 3,850,770 | 11/1974 | Juna et al. | 204/159.19 |
| 3,852,220 | 12/1974 | Kimmel et al. | 252/524 |
| 3,860,673 | 1/1975 | Lawrence | 260/859 R |
| 3,872,035 | 3/1975 | Papa et al. | 260/2.5 AW |
| 3,876,728 | 4/1975 | Kuroda et al. | 260/859 R |
| 3,884,917 | 5/1975 | Ibbotson | 260/248 NS |
| 3,914,335 | 10/1975 | Tugukuni et al. | 260/859 R |
| 3,925,335 | 12/1975 | Kuehn | 260/859 R |
| 3,926,875 | 12/1975 | Tsugukuni et al. | 260/23 TN |
| 3,932,401 | 1/1976 | Berg et al. | 260/248 NS |
| 3,943,075 | 3/1976 | Fishbein et al. | 260/2.5 AW |

FOREIGN PATENT DOCUMENTS

| | | | |
|---|---|---|---|
| 816,888 | 4/1974 | Belgium | 260/77.5 |
| 629,015 | 9/1949 | United Kingdom | 260/77.5 |
| 809,809 | 3/1959 | United Kingdom | 260/77.5 |

Primary Examiner—M. J. Welsh

[57] ABSTRACT

Process for the preparation of ethylenically unsaturated isocyanurates comprising reacting polyisocyanate with a monohydric alcohol containing a vinylidene group in the presence of a copper salt to form an isocyanate-containing urethane and then trimerizing the isocyanate-containing urethane to form an ethylenically unsaturated isocyanurate. The ethylenically unsaturated isocyanurate may be homopolymerized or copolymerized with ethylenically unsaturated monomers to form high molecular weight polymers having excellent physical properties.

31 Claims, No Drawings

PROCESS FOR PREPARING ETHYLENICALLY UNSATURATED ISOCYANURATES

This invention relates to a process for the preparation of ethylenically unsaturated isocyanurates. More particularly, this invention relates to a process for preparing an ethylenically unsaturated isocyanurate of a polyisocyanate and a monohydric alcohol containing a vinylidene group.

The expression "vinylidene group" when used in this application means the group characterized by the formula:

The expression "polyisocyanate" when used in this application means a compound containing 2 or more NCO groups.

The expression "allyl group" when used in the application means the group characterized by the formula:

The expression "aromatic polyisocyanate" when used in this application means a compound containing at least 2 isocyanate groups each of which is attached directly to the carbon atom of an aromatic ring.

The expression "isocyanurate" means a compound containing the structure:

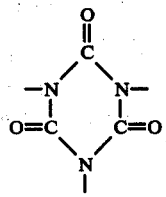

In accordance with the present invention, it has been found that ethylenically unsaturated isocyanurates may be prepared by a two-step process which comprises a first step of reacting a polyisocyanate with a monohydric alcohol containing a vinylidene group in the presence of a copper salt to form an isocyanate-containing urethane and a second step of trimerizing the isocyanate-containing urethane in the presence of an isocyanate trimerization catalyst to form an ethylenically unsaturated isocyanurate.

The isocyanurate compositions produced by the process of this invention may be monomeric, that is containing only one isocyanurate ring, or polymeric, that is containing more than one isocyanurate ring, but are usually mixtures of monomeric and polymeric species. Prior to curing, the solid isocyanurates of this invention are fusible, that is, they exhibit a softening point by the Ring and Ball method described in the A.S.T.M. Designation E28-58T.

The reaction of the polyisocyanate with the monohydric alcohol in the first step may be conducted in accordance with reaction conditions conventional in the prior art for reacting an alcohol with an isocyanate to form a urethane, provided that the reaction is carried out in the presence of a copper salt. It is essential, in accordance with the present invention, that the reaction of the monohydric alcohol with the polyisocyanate is carried out in the presence of a copper salt.

The copper salt used in the process of this invention may be any known copper salt, provided its anion does not interfere with the reaction. The presence of iodide anions in the reaction will not interfere with the preparation of the ethylenically unsaturated isocyanurate, but iodide anions may interfere with the curing of the ethylenically unsaturated isocyanurates and thus iodide anions are preferably avoided. The copper salt need not be soluble in the reactants or in any solvent which may be used. Although it is preferred to carry out the reaction of the polyisocyanate with the monohydric alcohol in an organic solvent and in the presence of a copper salt which is soluble in the solvent, it has been found that copper salts which are insoluble in the organic solvent or in the reactants may be used provided the reaction mixture is vigorously stirred. Apparently, the only requirement is that the copper salt be brought into intimate contact with the reactants. Illustrative examples of copper salts which may be used include cupric acetate, cupric benzoate, cupric glycinate, cupric acetylacetonate, cupric sulfate, cupric oxalate, cupric chloride, cupric bromide, cupric nitrate, cupric naphthenate, cupric formate, mono- and di-cupric salts of ethylenediaminetetraacetic acid, cuprous chloride, cuprous bromide, cuprous cyanide, and cupric propionate. Mixtures of more than one copper salt may also be used. A preferred catalyst is cupric acetate.

The use of copper salt in the process of this invention serves several beneficial purposes. The copper salt promotes the reaction of the aromatic polyisocyanate with the monohydric alcohol to form urethane, helps prevent undesirable reactions which lead to gelation, improves the storage stability of the unsaturated isocyanurate product, permits the development of low exotherms when polymerizing the unsaturated isocyanurate product, promotes the formation of polymerized isocyanurate products having excellent physical properties, and allows the reaction to proceed in a safe and reproducible manner.

The amount of copper salt used will depend on the particular copper salt selected and on the particular polyisocyanate and monohydric alcohol used. In general, the amount of salt employed is from 0.001% to 1%, based on the total weight of polyisocyanate and alcohol. A preferred amount of copper salt is from 0.02% to 0.2%. Lower amounts of copper salt are less effective and, for practical purposes, produce no increased benefits. Larger amounts of copper salt may be used, but do not increase benefits and may interfere with polymerization of the unsaturated isocyanurate.

The polyisocyanate used in the process of this invention may be any trimerizable polyisocyanate which is conventionally used in the art for the preparation of isocyanurates. For example, the polyisocyanate may be saturated, unsaturated, monomeric or polymeric. The only requirements are that the polyisocyanate contain at least two isocyanate groups, be trimerizable, and be free of any groups which interfere with the trimerization of isocyanate groups or which interfere in the reaction of an isocyanate group with hydroxyl group. Preferred isocyanates are aromatic isocyanates. Illustrative examples of polyisocyanates which are particularly useful include: 2,4-tolylene diisocyanate; 2,6-tolylene diisocyanate; m-phenylene diisocyanate; p-phenylene diisocyanate; 1,5-naphthalene diisocyanate; 4,4'-diphenyl ether diisocyanate; 4,4',4''-triphenylmethane triisocyanate; 2,4,4'-triisocyanatodiphenylmethane; 2,2',4-triisocyanato diphenyl; 4,4'-diphenylmethane diisocyanate; 4,4'-benzophenone diisocyanate; 2,2-bis(4-isocyanatophenyl)propane; 1,4-naphthalene diisocyanate; 4-methoxy-1,3-phenylene diisocyanate; 4-chloro-1,3-phenylenediisocyanate; 4-bromo-1,3-phenylene diisocyanate; 4-ethoxy-1,3-phenylene diisocyanate; 2,4'-diisocyanatodiphenyl ether; 4,4'-diisocyanatodiphenyl; 9,10-anthracene diisocyanate; 4,6-dimethyl--1,3-phenylene diisocyanate; 4,4'-diisocyanatodibenzyl; 3,3'-dimethyl-4,4'-diisocyanatodiphenylmethane; 3,3'-dimethyl-4,4'-diisocyanatodiphenyl; 3,3'-dimethoxy-4,4'-diisocyanatodiphenyl; 1,8-naphthalene diisocyanate; 2,4,6-tolylene triisocyanate; 2,4,4'-triisocyanatodiphenyl ether; diphenylmethane diisocyanate available under the trademarks Mondur and Papi, having a functionality of 2.1 to 2.7; 1,3-xylene 4,6-diisocyanate; aromatic isocyanate terminated polyurethanes; aromatic isocyanate terminated prepolymers of polyesters; 1,6-hexamethylene diisocyanate; ethylene diisocyanate; propylene 1,2-diisocyanate; butylene 1,2-diisocyanate; butylene 2,3-diisocyanate; pentamethylene diisocyanate; cyclopentylene 1,3-diisocyanate; cyclohexylene 1,2-diisocyanate; cyclohexylene 1,3-diisocyanate; cyclohexylene 1,4-diisocyanate; 1,10-decamethylene diisocyanate; diisocyanato dicyclohexyl methane; 1,5-diisocyanato-2,2-dimethyl pentane; hydrogenated 4,4'-diphenylmethane diisocyanate; hydrogenated tolylene diisocyanate; (OCNCH$_2$CH$_2$)$_2$S; (OCNCH$_2$CH$_2$CH$_2$)$_2$O; OCNCH$_2$CH$_2$CH$_2$CH(OCH$_3$)CH$_2$CH$_2$NCO; OCNCH$_2$CH$_2$CH$_2$O(CH$_2$)$_4$OCH$_2$CH$_2$CH$_2$NCO;

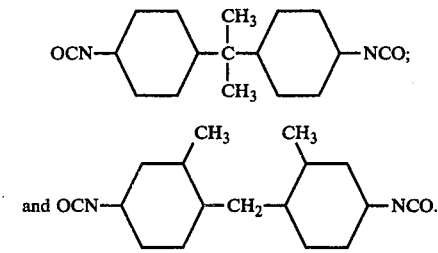

Preferred aromatic polyisocyanates are 2,4-tolylene diisocyanate, 2,6-tolylene diisocyanate, 4,4'-diphenylmethane diisocyanate, diphenylmethane polyisocyanates having an average functionality of 2.1 to 2.7, and mixtures thereof.

The monohydric alcohols which are useful in the process of this invention include any monohydric alcohol containing a vinylidene group but which does not contain an allyl group and, except for the alcoholic hydrogen, is free of radicals reactive with isocyanate groups. Illustrative examples of such alcohols include 4-vinylbenzyl alcohol, hydroxypropyl methacrylate, hydroxyethyl methacrylate, hydroxyethyl acrylate, hydroxypropyl acrylate, pentaerythritol triacrylate, pentaerythritol trimethacrylate, 8-hydroxyoctyl acrylate, 12-hydroxydodecanyl acrylate, 2-hydroxy-3-chloropropyl acrylate, 2-hydroxy-3-acryloyloxypropyl acrylate, 2-hydroxy-3-phenoxypropyl acrylate, 2-hydroxy-3-(o-chlorophenoxy)propyl acrylate, 2-hydroxy-3-(2,4-dichlorophenoxy)propyl acrylate, 2-hydroxy-3-propionyloxypropyl acrylate, 2-hydroxy-3-(2,4-dichlorobenzoyloxy)propyl acrylate, 2-hydroxy-3-cinnamoyloxypropyl acrylate, ethoxylated and propoxylated ethers of any of the foregoing alcohols, monohydroxy esters of a polyol and acrylic acid or methacrylic acid, for example, dibromoneopentyl glycol monoacrylate and monomethacrylate, mono acrylate and mono methacrylate esters of alkoxylated bisphenol A and of alkoxylated tetra bromobisphenol A, and polyoxyethylene and polyoxypropylene ethers of monohydric phenols. In the case of polyfunctional acrylates, it is preferred to use them in combination with monofunctional acrylates and methacrylates to help minimize high working viscosities and possible gelation problems during the reaction. Mixtures of monohydric alcohols containing a vinylidene group may also be used. A preferred class of vinylidene alcohols are the ester alcohols, particularly the acrylates and methacrylates, containing one vinylidene group. Preferred alcohols include hydroxypropyl methacrylate, hydroxyethyl methacrylate, hydroxyethyl acrylate, and hydroxypropyl acrylate.

While it is preferred that all the monohydric alcohols used in the process of this invention contain a vinylidene group and are free of allyl groups, it is contemplated by the present invention that a minor amount of such alcohols may be replaced with other hydroxyl containing compounds, such as other monohydric alcohols, dihydric alcohols, monohydric phenols, or dihydric phenols. Although it has been found that the high temperature properties decrease as the amount of the monohydric alcohol containing a vinylidene group decreases, one may be willing to sacrifice somewhat on the high temperature properties in order to introduce other desirable properties. For example, in some applications, one may be willing to sacrifice some high temperature properties for the inclusion of flame-retardancy or low smoke properties. The flame-retardancy properties may be introduced by substituting a minor amount of the monohydric vinylidene alcohol with a phosphorus or halogen containing alcohol or phenol. Similarly, low smoke properties may be introduced by substituting a minor amount of the monohydric, vinylidene alcohol with sulphur containing alcohols or phenols. Saturated monohydric alcohols are particularly useful with polyisocyanates having a functionality greater than two in order to limit the degree of branching in the unsaturated isocyanurate.

Illustrative examples of monohydric alcohols which may be used to replace up to 49 mol percent of the monohydric alcohol containing a vinylidene group described above include: methanol, ethanol, propanol, butanol, isopropanol, isobutanol, octyl alcohol, cyclohexanol, benzyl alcohol, allyl alcohol, glycerol diallyl ether, trimethylolpropane diallyl ether, saturated halogenated alcohols, halogenated alcohols containing ethylenic unsaturation, halogenated allyl alcohols, halogenated monohydric alcohols such as 2-bromo ethanol, 3-bromo-1-propanol, 4-chloro-1-butanol, 2-chlorethanol, 4-chloro-1-hexanol, 3-chloro-1-propanol, 2,3-dibromo-1-propanol, 2,3-dichloro-1-propanol, 2,2,2-trichloroethanol, 1-bromo-2-propanol, 1-chloro-2-propanol, 1,3-dibromo-2-propanol, and 1,3-dichloro-2-propanol.

Illustrative examples of dihydric alcohols which may be used to replace up to 33 mol percent, and preferably up to 10 mol percent, of the monohydric alcohol containing a vinylidene group described above include: ethylene glycol, propylene glycol, polyethylene glycol, polypropylene glycol, compounds characterized by the formula:

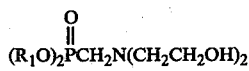

wherein $R_1$ is an alkyl group containing from 1 to 4 carbon atoms, 1,4-butane diol, pentamethylene glycol, hexamethylene glycol, glycerol methyl ether, glycerol monochlorohydrin, glyceryl monostearate, and dihydroxy acetone.

In general, phenols in small amounts (up to about 20%) that are reactive with aromatic isocyanates may be used in the practice of this invention. When reactive phenols are used, it is particularly important that essentially all of the phenolic hydroxyl groups are reacted with isocyanate groups so that unreacted hydroxyl groups will not be available to interfere with subsequent free radical curing reactions. Phenols such as 4-hydroxyphenyl-4'-chlorophenyl sulfone are especially useful because they characteristically improve the fire retardant and smoke properties of the product while still retaining elevated temperature retention of physical properties. Phenol may also be used to block a minor portion of the isocyanate functionality which may later be regenerated at elevated temperatures to produce products with improved bonding to a substrate, especially glass fibers. Nitrophenols do not react readily with isocyanates and are not within the scope of this invention.

The reaction of the polyisocyanate with the monohydric alcohol may be carried out at a temperature from about 10° C. to about 130° C., and preferably from about 40° C. to about 95° C. Lower temperatures result in a slow reaction whereas temperatures above about 95° C. may result in vinyl polymerization of the alcohol. It is preferred to run the urethane reaction at as low a temperature as possible in order to avoid vinyl polymerization of the alcohol. A primary alcohol reacts to form urethane at a lower temperature than a secondary or tertiary alcohol and an acrylate reacts at a lower temperature to give vinyl polymerization than a methacrylate. Thus a methacrylate of a secondary alcohol can be reacted at a relatively high temperature (reasonable rate of urethane formation, but no vinyl polymerization) but a primary alcohol acrylate requires a lower reaction temperature to avoid vinyl polymerization, but the primary alcohol group still undergoes the urethane reaction at a reasonable rate at the lower temperature.

The reaction of the polyisocyanate and the monohydric alcohol is continued until essentially all of the original hydroxyl groups have reacted. At this point, the reaction product is an isocyanate-containing urethane product containing from about 0.75 to about 1.6 moles of unreacted isocyanate groups for each mole of starting polyisocyanate used. The isocyanate-containing urethane product may be trimerized by any procedure conventional in the prior art for trimerizing isocyanates. A preferred method of trimerizing the isocyanate-containing urethane comprises maintaining the urethane reaction product at a temperature from about 0° C. to about 75° C., adding a trimerization catalyst, and maintaining the temperature from about 0° C. to about 95° C., and preferably from about 20° C. to about 60° C., and continuing the trimerization reaction until the isocyanate content has fallen to less than about 0.30%, and preferably less than 0.01%, by weight of the reaction mixture.

The trimerization catalyst used may be any trimerization catalyst known in the prior art for trimerizing isocyanates and which will not cause gellation of the isocyanurate. Illustrative examples of such catalysts include tertiary amines such as N,N-dimethyl aniline, N-methyl morpholine, triethylene tetramine, tributyl phosphine, and N-benzyltrimethylammonium hydroxide. The active trimerization catalyst is best employed in the range of from about 0.04% to about 1%, based on the total weight of isocyanate and alcohol used. Higher levels may present difficulties in the control of the exothermic trimerization, and lower levels may be either ineffective or delay completion of the reaction.

Although the process of this invention may be conducted in the absence of a solvent, it is preferred to carry out the urethane forming reaction and the trimerization reaction in the presence of a solvent for the reactants. When the trimerization reaction takes place in the absence of solvent, the product formed is invariably a solid and therefore requires special processing which permits the easy removal of the heat generated by the reaction and prevents the reaction mixture from reaching high temperatures which may induce insolubility and gelation of the products. Among these special processing techniques may be the trimerization of the monourethane in thin layers on moving temperature-controlled belts or in temperature-controlled trays. When solvent is used, it should be non-reactive, that is, the solvent should not contain any groups which would react with isocyanate groups or in any way interfere with the urethane forming reaction or the trimerization reaction. Thus, the solvent should not contain any hydroxyl, carboxy, or amine groups which might interfere with these reactions. This then limits the suitable solvents to esters, ethers, hydrocarbons and similar solvents containing non-reactive, non-functional groups. Illustrative examples of polymerizable solvents which may be employed in the first and second step of this process include styrene, methyl methacrylate, divinylbenzene, ethyl methacrylate, ethyl acrylate, methyl acrylate, 2-ethylhexyl acrylate, 2-ethylhexyl methacrylate, butyl acrylate, butyl methacrylate, isobutyl methacrylate, cyclohexyl methacrylate, cyclohexyl acrylate, chlorostyrene, acrylonitrile, vinylidene chloride, vinyl acetate, vinyl stearate, vinyltoluene, hexanediol diacrylate, hexanediol dimethacrylate, polyethylene glycol diacrylate, dimethylstyrene, ethylstyrene, propylstyrene, p-chloromethyl styrene, m-dibromoethylstyrene, bromostyrene, t-butyl styrene, vinyl propionate, vinyl butyrate, tetrahydrofurfuryl methacrylate, diethylene glycol diacrylate, triethylene glycol diacrylate, allyl methacrylate, diallyl fumarate, 1,3-butylene glycol dimethacrylate, polyethylene glycol diacrylate, tetramethylene glycol diacrylate, trimethylol propane triacrylate, neopentyl glycol diacrylate, and 1,3-butylene glycol diacrylate. Non-polymerizable solvents may also be used. Illustrative of such solvents include benzene, toluene, xylene, dioxane, methyl ethyl ketone, ethyl acetate, and ethyl benzene. The solvent may be removed when the reaction is complete to give a solid isocyanurate. The solid isocyanurate may be dissolved in the same or a different solvent when it is to be cured. Mixtures of solvents may also be used. A preferred class of solvents are those which contain at least one polymerizable double bond. A preferred solvent is styrene. Other preferred solvents are a mixture of styrene and methyl methacrylate and a mixture of styrene and divinylbenzene.

The amount of solvent employed in the process of this invention may vary over a rather wide range. The particular amount of solvent and the solvent used will depend somewhat of course on the nature of the solvent and on the solubility of the reactants used. For example, the reactants and the unsaturated isocyanurate products produced by the process of this invention are more soluble in polar solvents than in non-polar solvents. The amount of solvent used will also depend, in the case of those solvents containing polymerizable double bonds, on the nature of the properties desired in the final product. Thus, if one is interested in preparing the ethylenically unsaturated isocyanurate of toluene diisocyanate and hydroxypropylmethacrylate in styrene solvent for example, the high temperature properties of the final product will increase as the concentration of the styrene decreases. In general, however, the amount of solvent used will be from 0 to 95% by weight, and preferably from 30% to 80% by weight, based on the total weight of the reaction mixture.

The solution viscosity of the isocyanurates of this invention can be varied over a wide range by adjusting the stoichiometry of the aromatic poyisocyanates and vinylidene carbonyl oxy alcohols employed in their synthesis and/or the temperature of the trimerization. Thus by varying the degree of the excess isocyanate groups compared to hydroxyl groups it is possible to adjust the formation of high molecular weight species and solution viscosities at a fixed concentration. Increasing the excess of isocyanate groups compared to hydroxyl groups favors higher molecular weight species and therefore higher viscosities, conversely lowering the excess isocyanate groups compared to hydroxyl groups favors lower molecular weight species and therefore lower viscosities. By appropriate adjustment of this excess a curable resin solution of the desired viscosity can be obtained. This may be done by experiment, realizing that higher solids concentration, and higher reaction temperatures also lead to resins of increased solution viscosity. The converse of this is also true. The excess of moles of NCO groups compared to moles of —OH per mole of poyisocyanate should be kept in the range from about 0.75 to about 1.6, and preferably from about 0.9 to about 1.4. In a solution comprising equal parts of solvent and a mixture of hydroxypropylmethacrylate and toluenediisocyanate, the preferred excess for laminate applications is from about 0.95 to about 1.05.

The solution viscosity is increased as the temperature used in the trimerization reaction increases, but temperature variation is not as important a variable as the excess of isocyanate groups compared to hydroxyl groups. However, the trimerization temperature must be maintained from about 0° C. to about 95° C., since too high a temperature will cause the vinylidene group to polymerize prematurely.

Generally, as the solid content of the resin system decreases so does the solution viscosity, and to compensate for this reduction in viscosity which may make preparation of laminates a difficult task, the amount of high molecular weight polyisocyanurate structures is increased by increasing the excess of isocyanate groups to hydroxyl groups. The amount of these species may also be controlled by adjusting the trimerization temperature. As the solids levels decrease below 30% then extra care is needed with regard to the temperature profile. In some cases it may be necessary to alter the character of the solvent to keep the high molecular weight species in solution.

The following Table I illustrates ways to obtain vinylidene carbonyl oxy alkanol containing urethane isocyanurate solutions over a broad viscosity range. Although the table refers to the reaction products from hydroxypropylmethacrylate (HPMA) and toluene diisocyanate (TDI) dissolved in styrene, those skilled in the art will understand that similar relationships hold true for other solvent systems using other polyisocyanates or vinylidene alcohols. The examples in Table I illustrate the effect of the three important reaction parameters on the viscosity of the final product. Examples F and G as well as H and I show the effect of trimerization temperature on the viscosity of the final product. Examples D and F and J and L illustrate the effect of concentration on the viscosity, whereas, examples B and C, E, F, and I and also J and K demonstrate the effect of the molar excess of NCO groups compared to hydroxyl groups per mole of polyisocyanate, on the viscosity of the final product. All reactions listed in the table were carried to completion, i.e., the residual isocyanate content was essentially zero. Additional viscosity control may be achieved also by stopping the reaction short of completion as can be done in the usual manner by adding active hydrogen compounds compatible with the system and/or destruction of the trimerization catalyst. All reaction runs are in styrene using HPMA and TDI. Reaction runs B through L were made using the procedure outlined in example 1 whereas reaction run A was made according to the procedure outlined in example 8. The procedure used for run A involves a somewhat different mode of addition of polyisocyanate than used in runs B through L and is used primarily for the synthesis of low concentration products.

TABLE I

| | Moles (NCO)-Moles(OH) / Moles Polyisocyanate | % Styrene | Trimerization Temperature (° C) | Final Visc.[1] (cps) |
|---|---|---|---|---|
| A | 1.26 | 75 | 30 | 998(22.4° C) |
| B | 1.16 | 70 | 45 | 395 |
| C | 1.20 | 70 | 45 | 10,000 |
| D | 1.10 | 60 | 55 | 370 |
| E | 1.22 | 50 | 55 | 17,000 |
| F | 1.10 | 50 | 55 | 2,200 |
| G | 1.10 | 50 | 25 | 1,050 |
| H | 1.00 | 50 | 75 | 790 |
| I | 1.00 | 50 | 55 | 450 |
| J | 0.95 | 40 | 55 | 1,400 |
| K | 0.91 | 40 | 55 | 800 |
| L | 0.97 | 30 | 55 | 66,000 |

[1]Determined on a Brookfield Viscometer, Model LVT, #2 spindle, at 30 rpm. at 25° C.

When the ethylenically unsaturated isocyanurates prepared by the process of this invention are to be used shortly after their preparation, the addition of stabilizers is not necessary. However, when it is desired to store the isocyanurates for a long period of time, it may be desirable to add a chemical compound which will react with the trimerization catalyst or to add a stabilizer to prevent polymerization through the ethylenic double bond or reaction of any residual isocyanate groups which may be present in the isocyanurate product.

Exemplary of compounds which may be added to the final reaction product to neutralize the trimerization catalyst include acids such as acetic, phosphoric, sulfuric, oxalic, methanesulfonic, maleic, fumaric, acrylic, phthalic, isophthalic, and pyromellitic acids. The use of methanesulfonic acid or a mixture of methanesulfonic acid and oxalic acid are preferred. The amount of acid to be added varies with the particular isocyanurate and percent of isocyanurate in solution. Generally the amount of acid should range between about 50 and 200 mole percent, and preferably from about 100 to about 175 mole percent, of the trimerization catalyst used. If the combination of methanesulfonic acid/oxalic acid is used, the amount of oxalic acid should be in the range of 0.02 to 0.05 weight percent based on the total weight of isocyanurate solution.

The addition of an acid to neutralize the trimerization catalyst is effective to impart extended shelf life to the isocyanurate products of this invention, particularly in the case of isocyanurate solutions containing at least 40% by weight of dissolved solids. Levels of residual isocyanate content of up to 0.15% and even up to 0.2% at the time the trimerization reaction is terminated with an acid, such as methane sulfonic acid, do not cause serious stability problems. However, it has been found that levels of isocyanate content above 0.1% in isocyanurate solutions having a concentration of less than 40% by weight of dissolved solids at the time the trimerization reaction is terminated with the addition of the acid, may adversely affect the shelf stability of the isocyanurates. For this reason it may be desirable for the shelf life of these low solids solutions to reduce the residual NCO to levels below 0.1% through the addition of small amounts of compounds with labile hydrogen which react with NCO, such as alcohols and primary or secondary amines. Low molecular weight alcohols such as methanol, ethanol, propanols, and butanols and secondary amines are preferred. Dibutyl amine is the most preferred of those compounds. These labile hydrogen containing compounds are added to the resin solution at the end of trimerization reaction and prior to the acid addition in amounts equivalent to or slightly higher than the residual NCO at that point.

In order to avoid premature polymerization of the polymerizable materials used in the process of this invention or the resulting ethylenically unsaturated isocyanurates, a small amount of a conventional polymerization inhibitor, such as hydroquinone, tertiary butyl catechol, methyl ether of hydroquinone, and the like should be incorporated in the reaction mixture prior to reaction.

The unsaturated isocyanurate compositions prepared by the process of this invention and solutions thereof in copolymerizable solvent may be polymerized or cured in accordance with polymerization conditions conventional in the art for the polymerization of ethylenically unsaturated materials. In general, the polymerization may be carried out by reacting the unsaturated isocyanurate in the presence of a polymerization catalyst. Suitable polymerization initiators include the various peroxide initiators such as benzoyl peroxide, methyl ethyl ketone peroxide, di(2-ethylhexyl) peroxydicarbonate, t-butyl perbenzoate, dicumyl peroxide, and t-butyl hydroperoxide. Azo compounds, such as azobisisobutyronitrile may be used in combination with peroxide initiators. The amount of initiator employed is usually very small. For example, from about 1 part of initiator per 1000 parts of the polymerizable mixture to about 5 parts per 100 parts of said mixture.

In many applications, it is desirable to start the polymerization without the application of external heat. In such cases it is customary to add an accelerator to the system. Suitable accelerators include cobalt, manganese, lead, and iron compounds, such as cobalt naphthenate and manganese naphthenate, and tertiary amines such as dimethyl aniline.

The following are illustrative examples of peroxide-promoter combinations which may be added to the unsaturated isocyanurate compositions to achieve cure:

Formula I

1% Benzoyl peroxide
0.2% Dimethyl aniline

Formula II 0.02% Dimethyl aniline
0.06% Coblat naphthenate
2.0% Methyl ethyl ketone peroxide Formula III 0.03% Cobalt naphthenate
0.5% Acetylacetone peroxide (4% active oxygen)
1.5% t-butyl perbenzoate The isocyanurate product, particularly when prepared as a solution in a copolymerizable monomer, may contain any of the additives which are conventionally employed in polymerization systems, for example, antioxidants, U.V. absorbers, fillers, dyes and pigments.

Unsaturated isocyanurate products produced by the process of this invention have been found to be particularly useful in applications such as castings, coatings and laminates where it is desirable to have excellent combinations of flexural, tensile, and impact properties and good corrosion resistance at elevated temperatures. The products of this invention are particularly useful in a variety of filament wound products such as pipes, ducts, and storage tanks and in molded products where they may be combined with fillers and fibers.

The invention will be better understood from a consideration of the following examples which are presented for illustrative purposes and are not to be considered as defining or limiting the scope of this invention. All parts and percentages are by weight unless otherwise specified.

In the following examples, the castings and laminates are prepared as follows.

Castings are prepared by pouring the isocyanurate solution containing the curing reagents between two sheets of plate glass separated by a ⅛ inch polytetrafluoroethylene covered wire spacer. The curing reagents are added to the solution of isocyanurate in copolymerizable solvent by first adding the indicated promoter and accelerator to the isocyanurate solution and then adding the indicated peroxide. The casting is maintained at room temperature for 18–24 hours and then the resin is heated one hour at 100° C. in an oven to undergo postcuring;

Laminates are prepared by rolling the indicated isocyanurate solution containing the curing reagents evenly onto glass fiber mats with a paint-type roller then rolling thoroughly with a grooved laminating roller. The curing reagents are added to the solution of isocyanurate in copolymerizable solvent by first adding the indicated promoter and accelerator to the isocyanurate solution and then adding the indicated peroxide. ⅛ inch thick laminates are prepared with two layers of split strand 1½ ounce glass mats sandwiched between two 10 mil. surfacing "C" glass mats. The weight of the glass is 25% of the total resin glass weight. ¼ inch thick laminates are made by the following combination of glass mats impregnated with resin: 10 mil. surfacing "C" glass mat, two layers of 1½ ounce chopped strand mat, 1 layer woven roving, one layer of 1½ ounce chopped strand mat, 1 layer of woven roving and a final layer of 1½ ounce chopped strand glass mat. The amount of resin used to make this ¼ inch laminate is adjusted to give a resin ratio of 70%. Laminates are covered with a thin polyester film to exclude air from the surface during cure. After 18–24 hours at room temperature the cured laminates are heated for 1 hour at 100° C. in an oven for postcure.

In the following examples, the physical properties recited for the castings and laminates were obtained by the following ASTM test method:

| Physical Property | ASTM Test Method |
|---|---|
| Flexural strength | D 790 |
| Flexural modulus | D 790 |
| Tensile strength | D 638 |
| Tensile modulus | D 638 |
| % Elongation | D 638 |
| Izod Impact strength | D 256 |
| Barcol Hardness | D 2583 |
| Heat Deflection Temperature (264 psi) | D 648 |

EXAMPLE 1

A three-neck, round-bottom, 5-liter glass flask, equipped with thermometer, air inlet, dropping funnel, stirrer, and condenser is charged with 865 ml of hydroxypropyl methacrylate, 2144 ml of styrene, 1.8 g of cupric acetate, and 800 mg of hydroquinone. The solution is heated to 85° C., and 852 ml of toluene diisocyanate are slowly added over a 150 min. period. The temperature of the reaction medium during the addition of the toluene diisocyanate is maintained between 88° C. and 90° C. After the addition of the toluene diisocyanate is complete, the temperature of the reaction mixture is maintained at about 90° C. for an additional 90 min. The resulting dark green liquid is cooled to 55° C., and 5 ml of a 40% solution of benzyltrimethylammonium hydroxide dissolved in methanol is added over a 13 min. period. Heating is then continued at 55° C. for 2 hrs. to form an ethylenically unsaturated isocyanurate.

EXAMPLE 2

611.0 g of styrene, 33.1 g of hydroxypropyl methacrylate, 225 mg of cupric acetate, 100 mg of hydroquinone, are added to the reaction vessel described in Example 1. The resulting solution is heated to 90° C. while stirring vigorously. At this point, 34.8 g of toluenediisocyanate are added dropwise at a rate of approximately 6 to 10 ml/min. to the reaction flask. The temperature of the reaction medium is maintained at 90° C. until the addition of the toluenediisocyanate is complete and then for an additional 40 min. The resulting clear, emerald green solution is cooled to 55° C., and 1.5 ml of a 40% solution of benzyltrimethylammonium hydroxide and methanol is added. The solution remains unchanged for several minutes then begins to turn brown. The temperature of the solution is maintained at 55° C. until the isocyanate content falls to about 0. The resulting product is a styrene solution of the ethylenically unsaturated isocyanurate of toluene diisocyanate and hydroxypropyl methacrylate.

Examples 3–5 are prepared according to the process recited in Example 2 except that the amounts of styrene, hydroxypropyl methacrylate (HPMA), hydroxyethyl methacrylate (HEMA), and toluene diisocyanate (TDI) used are those indicated in the following Table Ia.

TABLE Ia

| Example Number | Styrene (grams) | HPMA (grams) | HEMA (grams) | TDI (grams) |
|---|---|---|---|---|
| 3 | 282 | 0 | 70.8 | 87 |
| 4 | 214 | 0 | 99.5 | 115.8 |
| 5 | 240 | 109.9 | 0 | 130.5 |

Example 6

According to the process of Example 1, 1314 grams of styrene, 232 grams of hydroxypropyl methacrylate, 4 ml. of a 10% solution of tertiary butyl catechol in styrene, and 920 milligrams of cupric acetate monohydrate are heated to 90° C. under an air sparge and nitrogen blanket and 335 grams of toluene diisocyanate (25% excess) are then added slowly over 60 minutes. The temperature is maintained at 90° C. during the addition and for 60 minutes afterward. The product is cooled to 41° C. and 5 ml. of 4% benzyltrimethylammonium hydroxide (Triton B) in methanol are added. The temperature is maintained at 45° C. for 4 hours. 5 ml. of tertiary butyl catechol (10% solution in styrene) and 1.05 ml. of methanesulfonic acid are added and the product is cooled. The resulting polymeric, ethylenically unsaturated polyisocyanurate contains a high proportion of product of molecular weight about 200,000 as determined by gel permeation chromatography. The viscosity after sitting overnight at room temperature is about 10,000 centipoise.

EXAMPLE 7

A 3-liter, 4-neck flask equipped with temperature control, air sparge, $N_2$ blanket, condenser, addition funnel, and stirrer is charged with 1254 grams of styrene, 227 grams of hydroxypropyl methacrylate (hydroxyl number 364), 460 milligrams of cupric acetate monohydrate, and 4.0 ml. of 10% tertiary butyl catechol (TBC) in styrene. The flask was then heated to 90° C. and 313 grams of toluene diisocyanate (TDI) is dripped in over a 55 minute period while the temperature is maintained at 90°–98° C. At the end of the TDI addition the temperature is maintained at 90° C. for an hour and a half, after which the solution is cooled to 45° C. 5 cc. of a 40% solution of benzyltrimethylammonium hydroxide in methanol is added. The resin turns very dark and an exotherm occurs which is controlled by means of a water bath so that the temperature does not exceed 50° C., and is restored to 45° C. and is maintained there. After 3.1 hours 1.20 cc. of methanesulfonic acid is added and a cooling water bath is applied. At 30° C. 5 ml. of 10% t-butyl catechol solution is styrene is added. At 25° C. the resin is poured into cans. The Brookfield viscosity is 395 cps. at 25° C. Physical properties are measured on a ⅛ inch casting that is postcured at 100° C. for 1 hour. The cure system comprises 100 grams resin, 0.4 gram dimethyl aniline, 0.5 gram cobalt naphthenate, 0.5 gram Lupersol 224 (acetylacetone peroxide solution), and 1.5 grams tertiary butyl perbenzoate. The casting (30% solids in styrene) has the following physical properties:

| | |
|---|---|
| Tensile modulus (psi) | 0.49 ± .03 × 10⁶ |
| Tensile strength (psi) | 10,900 |
| % Elongation | 2.58 |
| Flexural strength (25° C., psi) | 17,300 |
| Flexural modulus (psi) | 0.53 × 10⁶ |
| Heat distortion temperature | 111° C. |
| Unnotched izod impact | 2.91 |

EXAMPLE 8

A 3-liter, 4-neck flask is equipped with mechanical stirrer, thermometer, air sparge, reflux condenser, and N₂ inlet is charged with 171.0 grams hydroxypropyl methacrylate (1.14 equiv.), 1315.8 grams styrene (12.64 equiv.), 0.4535 gram Cu(OAc)₂.H₂O, and 3.75 ml. 10% tertiary butyl catechol (TBC) in styrene solution and the mixture is heated while stirring to 90° C. 206.9 grams toluene diisocyanate (TDI) (1.19 equiv.) is added dropwise over a 1 hour period, while maintaining the temperature at 90 ± 5° C. The reaction mixture is kept at 90 ± 5° C. for an additional hour, then cooled over a 1 hour period to 35° C. After adding 62.1 grams TDI (0.36 equiv.), it is cooled further to 30° C. 4.8 ml. benzyltrimethylammonium hydroxide (40% in MeOH) is then added, causing an exotherm which is controlled by use of a water bath. The trimerization reaction is terminated after 2.6 hours by addition of 14.9 grams dibutylamine; after 15 minutes, 1.49 ml. methanesulfonic acid (MSA) is added. The resulting product has a viscosity of 998 cps. at 22.4° C. A ⅛ inch casting is made and cured according to the method described in Example 7. The casting (25% solids in styrene) has the following properties:

| | |
|---|---|
| Tensile modulus (psi) | 0.55 × 10⁶ |
| Tensile strength (psi) | 9,400 |
| % Elongation | 2.28 |
| Flexural strength (psi) | 16,700 |
| Unnotched izod (ft-lbs) | 2.97 |
| Heat distortion temperature | 221° F. |
| Flexural modulus (psi) | 0.85 × 10⁶ |

EXAMPLE 9

Into a 3-liter, 4-neck flask equipped with mechanical stirrer, thermometer, air sparge, reflux condenser, and nitrogen inlet is charged methyl methacrylate (892 grams, 8.91 moles), hydroxypropyl methacrylate (414 grams, 2.78 moles), copper acetate monohydrate (0.403 gram), and 10% tertiary butyl catechol/styrene solution (4.0 cc.). The mixture is stirred and heated to 90° C., and toluene diisocyanate (TDI) (468 grams, 2.69 moles) added slowly over two hours while maintaining the temperature at 90° C. After all the TDI is added, the temperature is maintained at 90° C. for an hour while stirring and the reaction mixture is then cooled to 50° C. Triton B (40% benzyltrimethylammonium hydroxide in methanol) (5.0 ml.) is added. An exothermic reaction occurs and the temperature of the reaction mixture is maintained at 55° C. by external cooling. After keeping the mixture at 55° C. for two hours, it is then cooled to room temperature and 1.2 ml. methanesulfonic acid added. The resin has a viscosity of 1050 cps. at 23° C. A ⅛ inch casting is made and cured according to the method of Example 7. A ⅛ inch laminate is prepared using two plies of 1½ ounce chopped fiberglass strand mat between two 10 mil. surfacing "C" glass mats and cured at 100° C. for one hour. The casting and laminate have the following properties:

| | ⅛" Casting | 25% glass laminate ⅛" thick |
|---|---|---|
| Tensile modulus (psi) | 0.60 × 10⁶ | 1.41 × 10⁶ |
| Tensile strength (psi) | 8,500 | 14,800 |
| % Elongation | 1.65 | 1.47 |
| Flexural modulus (psi) | 0.60 × 10⁶ | 0.80 × 10⁶ |
| Notched izod (ft-lbs) | — | 5.51 |
| Heat deflection temperature | 266.9 ° F | — |
| Flexural strength (300° F., psi) | — | 14,000 |
| Flexural modulus (300° F., psi) | — | 0.51 × 10⁶ |
| Barcol (300° F) | — | 21–24 |
| Barcol (room temperature) | 55–62 | — |
| Flexural strength (psi) | 15,100 | 16,500 |

EXAMPLE 10

A 3-liter, 4-necked flask equipped with a mechanical stirrer, thermometer, air sparge, reflux condenser, dropping funnel and nitrogen inlet is charged with hydroxypropyl methacrylate (414 grams, 2.8 moles), styrene (772 grams, 7.4 moles), divinylbenzene (124 grams of a 72% active solution, 0.68 moles), cupric acetate monohydrate (0.45 gram), and 20% solution of tertiary butyl catechol in styrene (2 ml.). The mixture is heated to 40° C. and toluene diisocyanate (TDI) (80/20 mixture of 2,4- and 2,6-isomers, 486 grams, 2.8 moles) added over one hour. The reaction temperature is gradually increased to 90° C. by a combination of external heat and the exothermic nature of the reaction. The reaction mixture is kept at 90° for an additional hour and then cooled over ninety minutes to 45 ± 5° C. Triton B (40% solution of benzyltrimethylammonium hydroxide in methanol, 5 ml.) is then added and the exotherm controlled by use of a water bath. The reaction mixture is kept at 55 ± 5° C. for 2.5 hours and the trimerization reaction terminated by addition of methanesulfonic acid (1.2 ml.). The product has a viscosity of 1060 cps. at 21° C. A laminate is prepared and cured according to the method used in Example 9. The cured laminate has a flexural strength of 18,800 psi at room temperature and 11,100 psi at 350° F.

EXAMPLES 11–17

The procedure and apparatus of Example 1 are used in Examples 11–17. The indicated amount of toluene diisocyanate is added dropwise under a nitrogen blanket and air sparge to the copper catalyst, t-butyl catechol, and unsaturated alcohol in styrene at about 90° C. When the NCO content has dropped to about half the original content, the solution is cooled to about 55° C., Triton B added, and stirring is continued until the reaction is complete. The methanesulfonic acid and/or the TBC is then added to stabilize the product resin solution. The specific reactants, solvent, and catalysts used and the amounts thereof are shown in Table II.

TABLE II

| Ex. No. | Grams TDI | Grams Alcohol | Unsatd. Alcohol | Grams Solvent | Solvent | Grams Cupric Acetate Monohydrate | cc. 10% t-butyl catechol-styrene | cc. Triton B | cc. Methanesulfonic acid | % Solids | % Unreacted -NCO Group | Product Viscosity In cps at Room Temp. |
|---|---|---|---|---|---|---|---|---|---|---|---|---|
| 11 | 129 | 82.2 / 28.8 | HPMA / PETA | 358 | styrene | 0.23 | 1 | 1 | 0.3 | 40 | 3.9 | 28,000 (4) |
| 12 | 519.8 | 260 / 218 | HPMA / DBP | 1000 | styrene | 0.92 | 4 | 5+2+2 | 1.5 | 50 | 8.7 | — |
| 13 | 519.8 | 288 / 324.84 | HPMA / TBNA | 1134.8 | styrene | 1.09 | 5 | 5 | 1.5+ 5 TBC | 50 | 6 | 720 |
| 14 | 150.8 | 63.97 / 188 | HPMA (1) | 402.9 | styrene | 0.387 | 2 | 3 | — (3 TBC) | 50 | 7 | — |
| 15 | 173.2 | 72 / 400 | HPMA (2) | 616 | styrene | 0.597 | 3 | 3 | — (3 TBC) | 50 | 5 | 4400 (5) |
| 16 | 173.2 | 117.6 / 53.8 | HPMA (3) | 345.4 | styrene | 0.36 | 3 | 2 | 1+ 4 TBC | 50 | 2 | 1500 |
| 17 | 520 | 220.5 / 220.5 | HPMA / HEMA | 954.9 | styrene | 0.92 | 4 | 5 | — (5 TBC) | 50 | 0 | 360 |

HPMA = hydroxypropyl methacrylate
PETA = pentaerythritol triacrylate
DEP = 2,3-dibromopropanol
TBNA = tribromoeopentyl alcohol
HEMA = hydroxyethel methacrylate
= t-butylcatechol (10% in styrene)
Triton B = benzyltrimethylammonium hydroxide (40% in methanol)
TDI = toluene diisocyanate
(1) monomethacrylate of 2.2-polyoxypropylenebisphenol A
(2) monomethacrylate of 2,2-polyoxypropylene tetrabromobisphenol A
(3) 4-hydroxy-4′-chlorodiphenyl sulfone
(4) diluted with 26.25 g. HPMA and 17.4 g. styrene to 37% solids, viscosity 1150 cps
(5) diluted with 7.2 g. HPMA, viscosity 2600 cps

EXAMPLES 18–20

Examples 18–20 are prepared according to the process of Example 17 except that the indicated amounts of toluene diisocyanate, unsaturated alcohol, solvent and catalyst used are those indicated in Table III.

EXAMPLES 21–26

The procedure of Example 17 is used in Examples 21–26. The indicated reactants, catalysts and solvent and the amounts used are shown in Table IV.

TABLE III

| Ex. No. | Grams TDI | Grams Alcohol | Unsatd. Alcohol | Grams Solvent | Solvent | Grams Cupric Acetate Monohydrate | cc, 10% TBC-styrene | cc. Triton B | cc. MeSO$_3$H | % Solids | % Unreacted -NCO Group | Product Viscosity In cps at Room Temp. |
|---|---|---|---|---|---|---|---|---|---|---|---|---|
| 18 | 228.8 | 169.8 | HPA | 398.6 | styrene | 0.4 | (1) | 3 | — | 50 | 0 | 10,600 |
| 19 | 519.7 | 441 | HPMA | 700 / 262 | styrene / MMA | 0.92 | 4 | 5 | — (5 TBC) | 50 | 0 | 350 |
| 20 | 494 | 441 | HPMA | 307 | MMA | 0.92 | 4 | 5 | 1.5+ 5 TBC | 75 | 0 | (high)(2) |

TDI = toluene diisocyanate
TBC = t-butylcatechol (10% in styrene)
Triton B = benzyltrimethylammonium hydroxide (40% in methanol)
MeSO$_3$H = methanesulfonic acid
HPA = hydroxypropyl acrylate
HPMA = hydroxypropyl methacrylate
MMA = methyl methacrylate
(1) 200 mg. hydroquinone
(2) diluted with 252 g. MMA, viscosity 725 cps

TABLE IV

| Example Number | Grams Isocyanate | Isocyanate | Grams HPMA | Grams Styrene | Ratio Alc./-NCO | Grams Cupric Acetate Monohydrate | cc. 10% TBC in Styrene | cc. Triton B | % Un- cc. MeSO$_3$H | Viscosity % Solids | % reacted -NCO | Product In cps at Room Temp. |
|---|---|---|---|---|---|---|---|---|---|---|---|---|
| 21 | 176 | Mondur MR | 125 | 122 | 1:1.6 | 0.268 | 1 | 1 | 0.3+ 1 TBC | 50 | 5.6 | 495 |
| 22 | 184.2 | Isonate 125M | 115.8 | 298 | 1:1.9 | 0.23 | 1 | 0.5 | 0.2+ 1 TBC | 50 | 3.1 | 473 |
| 23 | 190.9 | Isonate 143I | 109.1 | 298 | 1:1.8 | 0.23 | 1 | 1 | 0.3+ 1 TBC | 50 | 1.5 | 1825 |
| 24 | 216.6 | Takenate 500 | 147.4 | 238 | 1:2.3 | 0.23 | 1 | 2 | 0.6+ 1 TBC | 60 | 6.5 | 305 |
| 25 | 238 / 213.2 | Mondur MR / TDI | 372.5 | 813 | 1:1.7 | 0.92 | 4 | 5 | — (6 TBC) | 50 | 3.0 | 1275 |
| 26 | 528 | PAPI | 400 | 928 | 1:1.6 | 0.84 | 3.6 | 5 | — | 50 | 5.2 | 135 |

TABLE IV-continued

| Example Number | Grams Isocyanate | Isocyanate | Grams HPMA | Grams Styrene | Ratio Alc./-NCO | Grams Cupric Acetate Monohydrate | cc. 10% TBC in Styrene | cc. Triton B | % Un-cc. MeSO₃H | Viscosity % Solids | % reacted -NCO | Product In cps at Room Temp. |
|---|---|---|---|---|---|---|---|---|---|---|---|---|
|  |  |  |  |  |  |  | (4 TBC) |  |  |  |  |  |

HPMA = hydroxypropyl methacrylate
TBC = t-butylcatechol (10% in styrene)
Triton B = benzyltrimethylammonium hydroxide (40% in methanol)
MeSO₃H = methanesulfonic acid
Mondur MR = diphenylmethane contg. 2.6 isocyanate groups avg.
Isonate 125 M = diphenylmethane contg. 2.0 NCO groups avg.
Isonate 143L = diphenylmethane contg. 2.1 NCO groups avg.
Takenate 500 = 1,3-xylene-4,6-diisocyanate.
TDI = toluene diisocyanate
PAPI = polyphenylenepolymethylene polyiscyanate contg. 2.2 NCO groups avg.

EXAMPLES 27-34

The isocyanurate products of Examples 27-34 are prepared according to the procedure of Example 1, except for the variations in reactants, solvent and catalysts indicated in Table V.

addition the temperature is lower or higher than 90° external heating or cooling is applied respectively to bring the temperature to about 90° C. The reaction mixture remains at about 90° C. for at least one hour after the total amount of TDI has been added and until the NCO content of the reaction mixture drops to

TABLE V

| Ex. No. | Grams TDI | Grams HPMA | Grams Styrene | Grams Copper Salt | Copper Salt | cc. 10% TBC in styrene | Trimerization Catalyst | Trimerization Catalyst | cc. MeSO₃H | % Solids | % Unreacted -NCO Group | Product Viscosity In cps at Room Temp. |
|---|---|---|---|---|---|---|---|---|---|---|---|---|
| 27 | 170.5 | 147 | 318.3 | 0.307 | chloride | 1 | 1 cc. | Triton B | 0.3 | 50 | 4.6 | 222.5 |
| 28 | 520.2 | 441 | 962 | 1.0 | naphthenate | 4 | 5 cc. | Triton B | — (5 TBC) | 50 | 2.3 | 1600 |
| 29 | 161.1 | 138.9 | 298 | 0.72 | nitrate | 1 | 5 cc. | Triton B | 1.5 | 50 | 0.33 | 395 |
| 30 | 520.2 | 441 | 954.9 | 0.92 | acetate | 4 | 2.5 cc. | Polycat 41 | — (5 TBC) | 50 | 6.2 | 800 |
| 31 | 130 | 110 | 238.7 | 0.92 | acetate | 1 | 1.25 cc. | Me₄N.OH | 0.375+ 1.25 TBC | 50 | 2.6 | 410 |
| 32 | 130 | 110 | 238.7 | 0.92 | acetate | 1 | 0.5 g. | Et₄N.O₂CH | 0.375+ 1.25 TBC | 50 | 3.1 | 280 |
| 33 | 520.2 | 440 | 961.6 | 0.92 | acetate | — (0.4 HQ) | 5 cc. | KOAc | — (0.5 HQ) | 50 | 0 | — |
| 34 | 520.2 | 441 | 954.9 | 0.92 | acetate | 2 | 2.0 g. | Et₄N.OAc | 1.5+ 2.5 TBC | 50 | 2.8 | 350 |

TDI = toluene diisocyanate
HPMA = hydroxypropyl methacrylate
MeSO₃H = methanesulfonic acid
Triton B = benzyltrimethylammonium hydroxide (40% in methanol)
Polycat 41 = a polyfunctional aliphatic tertiary amine (Abbott)
Me₄N.OH = tetramethylammonium hydroxide (40% in methanol)
Et₄N.O₂CH = tetraethylammonium formate
KOAc = potassium acetate
Et₄N.OAc = tetraethylammonium acetate
TBC = t-butylcatechol (10% in styrene)
HQ = hydroquinone

EXAMPLE 35

A preferred method of this invention is as follows. A chemical reactor equipped with agitator, condenser, gas pipe connections, vents, and port holes is first flushed with subsurface nitrogen. Subsequently an air sparge and nitrogen stream having relative flow rates of 1 to 3 are introduced into the reactor. 2.7 parts of hydroxypropylmethacrylate (HPMA) are then charged to the reactor. The air sparge and nitrogen streams are temporarily turned off and 0.0029 part of copper acetate monohydrate and 0.012 part of 20% solution of tertiary butyl catechol (TBC) in styrene are charged to the reactor under continuous agitation. The air sparge and nitrogen blanket streams are turned on again and 5.7 parts of styrene are charged to the reactor. The reaction mixture is then heated to about 40° C. When the temperature of the reaction mixture reaches 40° C. the incremental addition of an 80/20 mixture of 2,4- and 2,6-toulene diisocyanates (TDI) starts. An overall amount of 3.1 parts of TDI are charged over about one hour period. During this period the exotherm of the reaction of TDI with the alcohol raises the temperature of the reaction mixture to about 90° C. If at the end of the TDI addition the temperature is lower or higher than 90° external heating or cooling is applied respectively to bring the temperature to about 90° C. The reaction mixture remains at about 90° C. for at least one hour after the total amount of TDI has been added and until the NCO content of the reaction mixture drops to below 4.5% by weight. After both conditions are met the reaction mixture is cooled to about 50° C. 0.018 part of 40% solution of benzyltrimethylammonium hydroxide in methanol (Triton B) (a trimerization catalyst), are then added to the reaction mixture. Soon after the addition of Triton B an exothermic reaction starts during the duration of which the temperature of the reaction mixture is maintained between 50-60° C. From the time the exotherm appears the viscosity and NCO content of the reaction mixture are monitored very closely. When the viscosity of the reaction mixture reaches 400-500 cps and the NCO level drops to below 0.2% based on total weight of solution, 0.007 part of methanesulfonic acid are added to the reaction mixture and the mixture is then cooled. When the temperature reaches about 35° C., 0.014 part of TBC are added and the reaction is then cooled to room temperature. The resulting vinyl isocyanurate is clear, has a light yellow brown color, a viscosity of about 400-500 cps and a shelf life longer than 3 months.

The reaction product has a number average molecular weight of about 1160, a weight average molecular weight of about 2000, and a polydispersity of about 1.9. About 95% of the isocyanurates present have a molecular weight of below about 5200 and contain some isocyanurates having a molecular weight above 5200 and below about 26,000. This product corresponds to a product of formula II above where the number of isocyanurate rings in most of the isocyanurate molecules is less than 10. This product has a ball and ring melting point of about 95° C. and a viscosity of about 400–600 cps at 25° C., and a refractive index of about 1.557 $N_D^{20}$. The infrared spectrum of this product shows absorption bands characteristic of isocyanurates and the essential absence of isocyanate functionality. The hydroxyl number of the product is essentially zero.

⅛inch 2-ply laminates prepared from this resin retain more than 80% of their room temperature flexural and tensile strength at 300° F. The curing reagents used to cure the resin are 0.2% dimethyl aniline, 0.2% of a 10% solution of tertiary butyl catechol in styrene, and 2.0% benzoyl peroxide (50% active).

EXAMPLE 36

To a solution of 307 grams of a mixture of 1- and 2-hydroxydecyl methacrylate in 481 grams methyl methacrylate is added 0.3 grams of cupric acetate monohydrate and 1.3 ml. of 10% solution of t-butyl catechol in methyl methacrylate. The solution is heated to 90° C. and 174 grams of toluene diisocyanate added during 30 minutes. The temperature is maintained at 90° C. for an additional one hour. The solution is cooled to 55° C. and 1.7 ml. of a 40% methanolic solution of benzyltrimethylammonium hydroxide is added. The reaction is completed by heating for an additional 3 hours at 60° C. The reaction is terminated by the addition of 1.7 ml. 10% solution of t-butyl catechol in methyl methacrylate and 0.5 ml. methanesulfonic acid.

EXAMPLE 37

To a solution of 165 grams of 2-hydroxybutyl methacrylate in 71 grams of styrene is added 313 mg. of cupric acetate monohydrate and 0.75 ml. of a 10% solution in styrene of a 50/50 mixture of t-butyl catechol and mono-methyl ether of hydroquinone. The solution is heated to 90° C. and 174 grams of toluene diisocyanate is added over one hour. Heating at 90° C. is continued for one hour. The 268.3 grams of additional styrene is added, the solution cooled to 55° C., and 2.5 ml. of a 40% methanolic solution of benzyltrimethylammonium hydroxide added. The solution is maintained at 55° C. for one hour. The reaction is terminated by the addition of 1.3 ml. of a 10% solution in styrene of a 50/50 mixture of t-butyl catechol and mono-methyl ether of hydroquinone. The product has a viscosity of 200 cps at 25° C. Two-ply glass laminates (25% glass, 0.125 inch thick) of the resulting 50% resin solution in styrene and which are cured with 0.1% dimethylaniline, 0.5% acetylacetone peroxide solution (4% active oxygen), 1.5% tertiary butyl perbenzoate, and 0.1% of a 10% solution of tertiary butyl catechol in styrene, have the following physical properties measured at 300° F.: flexural strength 17,600 psi; flexural modulus 0.48 × 10⁶ psi; tensile strength 11,900 psi; tensile modulus 0.66 × 10⁶ psi; Barcol hardness 25–28; elongation 2.2%; notched Izod 4.05.

EXAMPLE 38

Into a 2-liter 3-neck flask equipped with mechanical stirrer, thermometer, and air sparge is charged toluene diisocyanate (TDI) (80/20 mixture of 2,4- and 2,6-isomers, 342 ml., 2.44 mole) and the contents of the flask are heated to 55° C. A solution consisting of copper acetate monohydrate (0.4 grams) and 3.0 ml. of a 10% tertiary butyl catechol in toluene solution, w/w, in hydroxypropyl methacrylate (360 ml., 2.44 mole), having an acid number of 18, is added dropwise from an addition funnel over a period of 31 minutes into the TDI. 49.4% of the original isocyanate concentration remains unreacted (analysis by infrared spectrophotometer) while the resulting green mixture has a viscosity of 550 cps. 2.5 ml. of a 20% tertiary butyl catechol in toluene solution, w/w, and Triton B (40% benzyltrimethylammonium hydroxide in methanol) (0.8 ml.) are added to 150 grams of the above mixture at 40° C. The mixture is stirred vigorously and placed in a pan submerged in a constant temperature bath at 45° C. After 12 minutes bubbles begin forming on the surface of this green mixture and after 35 minutes the color begins changing to brown. Concurrently, the temperature rises to 84° C. in 16 minutes and the product solidifies. The product is allowed to cool to 40° C. and then removed from the pan to be ground into a fine powder. The product is then dissolved in an equal weight of styrene, 1.5% tertiary butyl perbenzoate, 0.5% of a 6% solution of cobalt naphthenate, and 0.4% dimethylaniline are added and then 0.5% of acetylacetone peroxide solution (4% active oxygen) is added to the solution. The solution containing the curing reagents is used for the preparation of a ⅛ inch laminate containing about 25% glass. The physical properties of the laminate are as follows:

| Property | Temperature | |
|---|---|---|
| | 73° F. | 300° F. |
| Tensile strength (psi) | 14,300 | — |
| Tensile modulus (psi) | 1.43 × 10⁶ | — |
| % Elongation | 1.26 | — |
| Flexural strength (psi) | 16,600 | 17,200 |
| Flexural modulus (psi) | 0.84 × 10⁶ | 0.45 × 10⁶ |
| Notched Izod (ft-lbs) | 4.5 | — |

A ⅛ inch casting prepared from the same 50% solution of the solid VIC resin in styrene exhibits a heat deflection temperature of 255° F.

EXAMPLE 39

A 3-liter, 4-neck flask equipped with mechanical stirrer, thermometer, air sparge, reflux condenser, nitrogen inlet, and two dropping funnels is charged with 954.9 grams of styrene, 4 ml. of 10% solution of t-butyl catechol in styrene and 920 mg. of cupric acetate. The mixture is heated to 65° C. and 426.4 ml. of toluene diisocyanate and 445 ml. of hydroxypropyl methacrylate added simultaneously over a one hour period. Heating is continued for an additional 1.5 hours at 65° C. The reaction mixture is then cooled to 55° C. and 5 ml. of 40% methanolic benzyltrimethylammonium hydroxide is then added and the exotherm controlled with a water bath. The reaction is terminated when, as indicated in the IR spectrum, over 99% of all isocyanate group has reacted. The trimerization is terminated by the addition of 1.5 ml. of methanesulfonic acid and the product is stabilized by the addition of 5 ml. of a 10% solution of t-butyl catechol in styrene. The product has a viscosity of 330 cps at 25° C. A laminate is prepared and cured according to the method used in Example 9. The cured laminate has a flexural strength of 20,200 psi at 300° F.

EXAMPLE 40

A four neck, 1000 ml. r.b. glass flask, equipped with stirrer assembly, pot thermometer, dropping funnel, air inlet and reflux condenser is charged with 24.6 ml. hydroxyethyl methacrylate, 243.2 grams benzene, 225 mg. cupric acetate, and 100 mg. hydroquinone. The reaction mixture is heated to 79° C. and 34.8 grams toluene diisocyanate added over a 15-minute period. Heating at 80° C. is continued for an additional 40-minute period. The product is then cooled to 55° C. and 1.5 ml. 40% methanolic benzyltrimethylammonium hydroxide added. The reaction is maintained at 55° C. for 52 minutes. The product is an olive green liquid. After solvent removal, the product is isolated as a light brown powder.

EXAMPLE 41

A 150 ml. resin kettle, equipped with immersed thermometer, air inlet, addition funnel, and mechanized stirrer assembly is charged with 100 ml. carbon tetrachloride, 14.4 ml. hydroxypropyl methacrylate, 20 mg. cupric acetate, and 75 mg. hydroquinone. The reaction mixture is heated to 77° C. and 14.2 ml. toluene diisocyanate added over 14 minutes. The product is maintained at 77° C. for an additional 31 minutes. To 10 ml. of this product, a clear yellow liquid, is added 2 drops of 40% methanolic benzyltrimethylammoniun hydroxide and the product is maintained overnight at room temperature. The reaction product in carbon tetrachloride is a yellow paste, showing only traces of an isocyanate peak.

EXAMPLE 42

The procedure and apparatus of Example 1 are used herein. Into a solution of 955 grams styrene are charged 441 grams hydroxypropyl methacrylate, 920 mg. cuprous chloride, and 4 ml. of a 10% solution in styrene of t-butyl catechol. The solution is heated to 90° C. and 426.4 ml. toluene diisocyanate added dropwise over one hour. The reaction is maintained at 90° C. for an additional 40 minutes, and then cooled to 55° C. Thereupon 5 ml. of a 40% methanolic solution of benzyltrimethylammonium hydroxide is added, the exotherm controlled, and the reaction mixture maintained at 55° C. for 2 hours and 25 minutes. The product, a clear amber brown liquid, is cooled and stabilized by the addition of an additional 5 ml. t-butyl catechol solution, and 1.5 ml. of methanesulfonic acid.

Although the process of this invention has been described with reference to specific reactions, conditions and reactants, it will be apparent that still other different and equivalent reactants and process conditions may be substituted for those specifically described, all within the sphere and scope of this invention.

Having described the invention, what is desired to be secured by Letters Patent is:

1. A process for preparing an ethylenically unsaturated isocyanurate which comprises reacting a polyisocyanate with a monohydric alcohol which contains a vinylidene group and which does not contain an allyl group, in the presence of a copper salt to form an isocyanate-containing urethane, wherein the amounts of monohydric alcohol and polyisocyanate are selected to furnish after said reaction from 0.75 to 1.6 moles of unreacted isocyanate groups per mole of polyisocyanate used, then adding a catalytic amount of an isocyanate trimerization catalyst which will initiate trimerization of the isocyanate-containing urethane without causing gellation, and trimerizing the isocyanate-containing urethane to form an ethylenically unsaturated isocyanurate.

2. A process of claim 1 wherein the organic polyisocyanate is an aromatic polyisocyanate.

3. A process of claim 2 wherein the monohydric alcohol is hydroxypropyl methacrylate, hydroxypropyl acrylate, hydroxyethyl methacrylate, hydroxyethyl acrylate, pentaerythritol triacrylate, pentaerythritol trimethacrylate, or mixtures thereof.

4. A process of claim 3 wherein the aromatic isocyanate is tolylene diisocyanate.

5. A process of claim 4 wherein the copper salt is cupric acetate.

6. A process of claim 1 which comprises (a) preparing a solution of a copper salt, a free radical polymerization inhibitor, and a monohydric alcohol, said alcohol containing a vinylidene group, in a solvent which is unreactive with isocyanate groups, (b) slowly adding a trimerizable organic polyisocyanate to the solution in the presence of sufficient oxygen to keep the inhibitor active and while maintaining the temperature of the solution from 10° C. to 130° C. to form an isocyanate-containing monourethane, (c) adding a catalytic amount of a trimerization catalyst which will initiate trimerization of the monourethane without causing gellation of the monourethane, and (d) maintaining the temperature from 0° C. to 95° C. to form an isocyanurate.

7. A process of claim 6 wherein the organic polyisocyanate is an aromatic diisocyanate.

8. A process of claim 6 wherein the organic polyisocyanate is a tolylene diisocyanate.

9. A process of claim 7 wherein the alcohol is hydroxypropyl methacrylate.

10. A process of claim 7 wherein the alcohol is hydroxyethyl methacrylate.

11. A process of claim 7 wherein the alcohol is hydroxyethyl acrylate.

12. A process of claim 7 wherein the monohydric alcohol is hydroxypropyl acrylate.

13. A process of claim 7 wherein the alcohol is a mixture of hydroxypropyl methacrylate and hydroxyethyl methacrylate.

14. A process of claim 7 wherein the solvent is an aromatic hydrocarbon.

15. A process of claim 7 wherein the solvent is a vinylidene monomer.

16. A process of claim 7 wherein the solvent is selected from the group consisting of styrene, benzene, methyl methacrylate, divinylbenzene, ethyl methacrylate, dioxane, ethyl acrylate, ethyl acetate, and methyl ethyl ketone.

17. A process of claim 7 wherein the trimerization catalyst is tributyl phosphine.

18. A process of claim 7 wherein the trimerization catalyst is N-benzyltrimethylammonium hydroxide.

19. A process of claim 7 wherein the trimerization temperature is from 20° C. to 65° C.

20. A process of claim 7 wherein the amount of solvent is from about 30% to about 80% by weight of the weight of the total composition.

21. A process of claim 7 wherein the copper salt is cupric acetate.

22. A process of claim 20 wherein the monohydric alcohol is selected from the group consisting of hydroxypropyl methacrylate, hydroxyethyl methacrylate, hydroxyethyl acrylate, hydroxypropyl acrylate, and mixtures thereof, the solvent is styrene, the polyisocyanate is a tolylene diisocyanate, the copper salt is cupric acetate, the trimerization catalyst is N-benzyltrimethylammonium hydroxide, and the trimerization temperature is from 20° C. to 65° C.

23. A process of claim 22 wherein the monohydric alcohol is hyroxypropyl methacrylate, hydroxyethyl methacrylate or mixtures thereof.

24. A process of claim 23 wherein the free radical polymerization inhibitor is hydroquinone, tertiary butyl catechol, monomethyl ether or hydroquinone, or mixtures thereof.

25. A process of claim 1 wherein the trimerization catalyst is neutralized with an acid after the formation of the ethylenically unsaturated isocyanurate.

26. A process of claim 25 wherein the acid is methanesulfonic or a mixture of methanesulfonic acid and oxalic acid.

27. A process of claim 25 wherein a low molecular weight alcohol or secondary amine is added prior to the addition of the acid.

28. A process of claim 3 wherein the copper salt is a cupric salt.

29. A process of claim 3 wherein the copper salt is a cuprous salt.

30. A process of claim 3 wherein the urethane forming reaction and the trimerization reaction are conducted in the absence of a solvent.

31. A process of claim 1 wherein the monohydric alcohol contains an ester group.

* * * * *

UNITED STATES PATENT AND TRADEMARK OFFICE
CERTIFICATE OF CORRECTION

PATENT NO. : 4,128,537  
DATED : December 5, 1978  
INVENTOR(S) : Kenneth H. Markiewitz Page 1 of 2

It is certified that error appears in the above-identified patent and that said Letters Patent are hereby corrected as shown below:

Column 10, line 53, "follows." should read -- follows: --.
Column 12, line 61, "is" first occurrence should read -- in --.
Column 15, line 23, under TABLE II, "DEP =" should read -- DBP = --.
Column 15, line 24, under TABLE II, "tribromoeopentyl" should read -- tribromoneopentyl --.
Column 15, line 25, under TABLE II, before "= t-butylcatechol" insert -- TBC --.
Column 16, line 7, under TABLE II, column 13, "28,000" should read -- 20,000 --.
Column 15, line 11, under TABLE IV, column 3, "Isonate 1431" should read -- Isonate 143L --.
Column 16, line 4, under TABLE IV, column 10, delete "% Un-".
Column 16, line 4, under TABLE IV, column 11, delete "Viscosity".
Column 16, line 4, under TABLE IV, column 12, insert -- % Un- --.
Column 16, line 4, under TABLE IV, column 13, insert -- Viscosity --.

UNITED STATES PATENT AND TRADEMARK OFFICE
CERTIFICATE OF CORRECTION

PATENT NO. : 4,128,537

DATED : December 5, 1978

INVENTOR(S) : Kenneth H. Markiewitz

It is certified that error appears in the above-identified patent and that said Letters Patent are hereby corrected as shown below:

Column 18, line 4, under TABLE IV-continued, column 10, delete "% Un-".

Column 18, line 4, under TABLE IV-continued, column 11, delete "Viscosity".

Column 18, line 4, under TABLE IV-continued, column 12, insert -- % Un- --.

Column 18, line 4, under TABLE IV-continued, column 13, insert -- Viscosity --.

Signed and Sealed this

Twentieth Day of November 1979

[SEAL]

Attest:

RUTH C. MASON
*Attesting Officer*

LUTRELLE F. PARKER
*Acting Commissioner of Patents and Trademarks*